US012397004B2

(12) United States Patent
Pahan (10) Patent No.: US 12,397,004 B2
(45) Date of Patent: Aug. 26, 2025

(54) NASAL DELIVERY OF LOW-DOSE ASPIRIN FOR THE TREATMENT OF NEURODEGENERATIVE AND LYSOSOMAL STORAGE DISEASES

(71) Applicant: Rush University Medical Center, Chicago, IL (US)

(72) Inventor: Kalipada Pahan, Skokie, IL (US)

(73) Assignee: Rush University Medical Center, Chicago, IL (US)

( * ) Notice: Subject to any disclaimer, the term of this patent is extended or adjusted under 35 U.S.C. 154(b) by 837 days.

(21) Appl. No.: 17/290,798

(22) PCT Filed: Nov. 5, 2019

(86) PCT No.: PCT/US2019/059794
§ 371 (c)(1),
(2) Date: May 3, 2021

(87) PCT Pub. No.: WO2020/097028
PCT Pub. Date: May 14, 2020

(65) Prior Publication Data
US 2021/0401856 A1  Dec. 30, 2021

Related U.S. Application Data

(60) Provisional application No. 62/755,695, filed on Nov. 5, 2018.

(51) Int. Cl.
*A61K 31/616* (2006.01)
*A61K 9/00* (2006.01)
*A61P 25/28* (2006.01)

(52) U.S. Cl.
CPC .......... *A61K 31/616* (2013.01); *A61K 9/0043* (2013.01); *A61K 9/0078* (2013.01); *A61P 25/28* (2018.01)

(58) Field of Classification Search
None
See application file for complete search history.

(56) References Cited

U.S. PATENT DOCUMENTS

| 4,885,287 A * | 12/1989 | Hussain | A61P 7/02 |
| | | | 514/159 |
| 2002/0025917 A1 | 2/2002 | Pappalardo | |
| 2014/0322328 A1 | 10/2014 | Yadidi | |
| 2015/0359851 A1 | 12/2015 | Stankovic et al. | |
| 2017/0027963 A1 | 2/2017 | Crowley et al. | |
| 2017/0354666 A1 | 12/2017 | Pahan | |

FOREIGN PATENT DOCUMENTS

EP  0504263 A1  9/1992

OTHER PUBLICATIONS

McLean, Journal of Allergy and Clinical Immunology, vol. 72, Issue 2, 1983, pp. 187-192 (Year: 1983).*

(Continued)

*Primary Examiner* — Jeffrey S Lundgren
*Assistant Examiner* — Anthony Joseph Seitz
(74) *Attorney, Agent, or Firm* — Barnes & Thornburg LLP (57) ABSTRACT

Provided herein are methods for delivering acetylsalicylic acid via nasal delivery for the treatment of neurodegenerative and lysosomal storage disorders, such as Alzheimer's disease and Batten disease.

8 Claims, 11 Drawing Sheets

(56) References Cited

OTHER PUBLICATIONS

Chen et al., Frontiers in Aging Neuroscience, vol. 6, Article 7, 2014 (Year: 2014).*

Bohnen et al., White matter lesions in Parkinson disease. Nat Rev Neurol. Apr. 2011;7(4):229-36 (Year: 2011).*

Smith et al., Neurobiology of Disease, vol. 36, Issue 2, 2009, pp. 242-251 (Year: 2009).*

Aubin N., Curet O., Deffois A., Carter C. (1998) Aspirin and salicylate protect against MPTP-induced dopamine depletion in mice. J Neurochem, 71, 1635-1642.

Berk M., Dean O., Drexhage H., McNeil J.J., Moylan S., O'Neil A., Davey C.G., Sanna L., Maes M. (2013) Aspirin: a review of its neurobiological properties and therapeutic potential for mental illness. BMC Med, 11, 74.

Chandra, S., Malabendu J., Pahan K. (2018) Aspiring induces Lysosomal biogenesis and attenuates Amyloid plaque pathology in a mouse model of Alzheimer's disease via a PPARα. J Neuroscience, 0054-18; DOI: https://doi.org/10.1523/JNEUROSCI.0054-18.2018.

Dai Y., Ge J. (2012) Clinical use of aspirin in treatment and prevention of cardiovascular disease. Thrombosis. 2012; 2012: 245037. Published online Nov. 2, 20114. doi: [10.1155/2012/245037].

De Duve, C. and Wattiaux, R. (1966) Functions of lysosomes. Annu Rev Physiol, 28, 435-492.

Djupesland, P.G. (2013) Nasal drug delivery devices: characteristics and performance in a clinical perspective—a review. Drug Deliv Transl Res. 3(1), 42-62.

Djupesland, P.G., Messina J.C., Mahmoud, R.A. (2014) The nasal approach to delivering treatment for brain diseases: an anatomic, physiologic, and delivery technology overview. Therapeutic Delivery, 5(6), 709-733.

El-Behi, M., Rostami, A., and Ciric, B. (2010) Current views on the roles of Th1 and Th17 cells in experimental autoimmune encephalomyelitis. J Neuroimmune Pharmacol, 5, 189-197.

Green GA (2001) Understanding NSAIDs: from aspirin to COX-2. Clin Cornerstone, 3, 50-60.

International Preliminary Report on Patentability, issued in PCT/US2019/059794, dated May 11, 2021.

International Search Report, issued in PCT/US2019/059794, dated Jan. 21, 2020.

Lanas A., and Scheiman J. (2007) Low-dose aspirin and upper gastrointestinal damage: epidemiology, prevention and treatment. Curr Med Res Opin., 23(1), 163-73.

Miyake et al., "The Blood-Brain Barrier and Nasal Drug Delivery to the Central Nervous System," American Journal of Rhinology & Allergy, vol. 29, Issue 2, (2015), pp. 124-127.

Mondal, S., Jana, M., Dasarathi, S., Roy, A., and Pahan, K. (2018) Low-dose aspirin ameliorates experimental allergic encephalomyelitis through interleukin-11-mediated protection of regulatory T cells. Sci. Signal., vol. 11, pp. 1-27.

Moyad M.A. (2001) An introduction to aspirin, NSAids, and COX-2 inhibitors for the primary prevention of cardiovascular events and cancer and their potential preventive role in bladder carcinogenesis: part II. Semin Urol Oncol, 19, 306-316.

Nagelschmitz et al., "First-in-Man Dose Escalation Study of Aspirin® Inhaled for the Clinical Development of a New Antiviral Treatment of Resistant Influenza," Clinical Therapeutics, vol. 37, Issue 8, Suppl. (2015), p. E155.

Nilsson S.E., Johansson B., Takkinen S., Berg S., Zarit S., McClearn G., Melander A. (2003) Does aspirin protect against Alzheimer's dementia? A study in a Swedish population-based sample aged > or =80. Eur J Clin Pharmacol, 59, 313-319.

Patel, D., Roy, A., Kundu, M., Jana, M., Luan, C.H., Gonzalez, F.J., and Pahan, K. (2018). Aspirin binds to PPARα to stimulate hippocampal plasticity and protect memory. Proc Natl Acad Sci, 115, E7408-E7417.

Perez-Sala et al. "The C-Terminal Sequence of RhoB Directs Protein Degradation through an Endo-Lysosomal Pathway," PLOS One, vol. 4, Issue 12, (2009), pp. 1-14.

Rangasamy, S. B., Dasarathi, S., Pahan, P., Jana, M., and Pahan, K. (2018) Low-dose aspirin upregulates tyrosine hydroxylase and increases dopamine production in dopaminergic neurons: Implications for Parkinson's disease. J. Neuroimmune Pharmacol. (In press; DOI: 10.1007/s11481-018-9808-3).

Rangasamy, S.B., Corbett, G.T., Roy, A., Modi, K.K., Bennett, D.A., Mufson, E.J., Ghosh, S., and Pahan, K. (2015) Intranasal Delivery of NEMO-Binding Domain Peptide Prevents Memory Loss in a Mouse Model of Alzheimer's Disease. J Alzheimers Dis, 47, 385-402.

Rizwan S., Idrees A., Ashraf M., Ahmed T. (2016) Memory-enhancing effect of aspirin is mediated through opioid system modulation in an AlCl3-induced neurotoxicity mouse model. Exp Ther Med, 11, 1961-1970.

Rothwell P.M., Wilson M., Price J.F., Belch J.F., Meade T.W., Mehta Z. (2012) Effect of daily aspirin on risk of cancer metastasis: a study of incident cancers during randomised controlled trials. Lancet, 379, 1591-1601.

Roy, A., Jana, M., Corbett, G.T., Ramaswamy, S., Kordower, J.H., Gonzalez, F.J., and Pahan, K. (2013) Regulation of cyclic AMP response element binding and hippocampal plasticity-related genes by peroxisome proliferator-activated receptor alpha. Cell Rep, 4, 724-737.

Roy, A., Jana, M., Kundu, M., Corbett, G.T., Rangaswamy, S.B., Mishra, R.K., Luan, C.H., Gonzalez, F.J., and Pahan, K. (2015) HMG-CoA Reductase Inhibitors Bind to PPARα to Upregulate Neurotrophin Expression in the Brain and Improve Memory in Mice. Cell Metab, 22, 253-265.

Sakaguchi, S. (2005) Naturally arising Foxp3-expressing CD25+ CD4+ regulatory T cells in immunological tolerance to self and non-self. Nat Immunol, 6, 345-352.

Sakaguchi, S., and Powrie, F. (2007) Emerging challenges in regulatory T cell function and biology. Science, 317, 627-629.

Sestini et al., "Different Effects of Inhaled Aspirinlike Drugs on Allergen-Induced Early and Late Asthmatic Responses," Am J Respir Crit Care Med., vol. 159, (1999), pp. 1228-1233.

Shi, G., Cox, C.A., Vistica, B.P., Tan, C., Wawrousek, E.F., and Gery, I. (2008) Phenotype switching by inflammation-inducing polarized Th17 cells, but not by Th1 cells. J Immunol, 181, 7205-7213.

Soleti et al., "Aspirin Inhalation Treatment for COPD Patients: Preliminary Studies on PK and Inflammatory Biomarkers," European Respiratory Journal, vol. 38, Suppl. 55, (2011), p. 825.

Sostres, C., Lanas, AI. (2011) Gastrointestinal effects of aspirin. Nat Rev Gastroenterol Hepatol, 8(7), 385-94.

"Abstracts from the Joint Meeting of the International Society for NeuroVirology (ISNV) and the Society on Neuroimmune Pharmacology (SNIP) Apr. 10-14, 2018, Chicago, Illinois, USA", Journal of Neurovirology, Informa Healthcare, Mar. 19, 2018, vol. 24, No. 1, pp. 1-102.

Extended European Search Report for European Application No. 19882244.7 dated Jun. 21, 2022.

* cited by examiner

NASAL DELIVERY OF LOW-DOSE ASPIRIN FOR THE TREATMENT OF NEURODEGENERATIVE AND LYSOSOMAL STORAGE DISEASES

CROSS REFERENCE TO RELATED APPLICATIONS

This application is a National Stage application of International Application No. PCT/US2019/059794, filed Nov. 5, 2019, which claims priority to U.S. Provisional Patent Application No. 62/755,695, filed Nov. 5, 2018, both of which are incorporated by reference herein in their entirety.

FEDERALLY SPONSORED RESEARCH OR DEVELOPMENT

This invention was made with government support under contract number AG050431 awarded by the National Institutes of Health, and contract number I01BX002174 awarded by the Department of Veterans Affairs. The government has certain rights in the invention.

TECHNICAL FIELD

The present invention relates to methods of delivering acetylsalicylic acid via nasal delivery for the treatment of neurodegenerative and lysosomal storage disorders, such as Alzheimer's disease and Batten disease.

BACKGROUND

Neurodegenerative diseases (NDs) encompass a wide variety of conditions that primarily cause the progressive death of neurons in the human brain. This cell death gives rise to the various neurological signs and symptoms unique to specific neurodegenerative disorders. The most common neurodegenerative disorders include Alzheimer's disease and related dementias, Parkinson's disease, multiple system atrophy (MSA), Lewy body dementia, multiple sclerosis (MS), and Huntington's disease. Lysosomes are membrane bound organelles containing several acid hydrolases that are responsible for degradation of lipid, protein, carbohydrates, and nucleic acids (De Duve and Wattiaux 1966). Defects and deficiencies in almost any of them results in accumulation of undigested/partially digested material in the lysosomes and forms the basis of numerous lysosomal storage disorders (LSDs) (De Duve and Wattiaux 1966, Perez-Sala et al. 2009), including Batten disease (infantile, late-infantile and juvenile), Niemann-Pick disease, Krabbe disease, Tay-Sachs disease, Sandhoff disease, Gaucher disease, Fabry disease, and Farber disease. With limited therapeutic options that are merely supportive or symptomatic for the treatment of these diseases, increasing life span and/or improving the quality of life in patients with NDs or LSDs is an important area of research, indicating an urgent need for novel therapeutic approaches.

Acetylsalicylic acid (AA), commonly known as aspirin, is one of the most frequently and widely used drugs available (Green, 2001). In addition to its extensive use as both an analgesic and antipyretic, aspirin has also been shown to provide beneficial effects against both cardiac diseases and cancers (Moyad, 2001; Dai and Ge, 2012; Rothwell et al., 2012; Berk et al., 2013). In addition, several studies have explored the neuroprotective effects of aspirin under different neurodegenerative disease conditions. Aspirin has been shown to have neuroprotective effects in animal models of Parkinson's disease (Aubin et al., 1998), and both memory enhancing effects (Rizwan et al., 2016) and maintenance of cognitive function in patients with Alzheimer's disease (Nilsson et al., 2003). Aspirin also lowers plaque pathology in a mouse model of Alzheimer's disease (Chandra et al., 2018). Moreover, low-dose aspirin has been found to suppress the development of experimental allergic encephalomyelitis (EAE) associated with MS (Mondal et al., 2018) and stimulate the production of dopamine associated with Parkinson's disease (Rangasamy et al., 2018).

Furthermore, even the standard dosage for baby aspirin at 81 mg is highly effective for long term, daily use in adults. Thus, the long history of aspirin as an analgesic coupled with its well-established safety profile make it appealing as a possible therapeutic for both neurodegenerative and lysosomal storage disorders.

However, despite this potential, the risk of gastrointestinal damage from aspirin use is prevalent, and even more so in adults with pre-existing conditions (Sostres et al., 2011). Even low-dose aspirin has been found to have similar side effects unless co-administered with proton pump inhibitors (PPIs) (Lanas et al., 2007).

Nasal delivery of drugs directly to the brain offers an alternative to traditional oral formulations that may be problematic in crossing the blood brain barrier, have limited bioavailability or cause gastrointestinal side effects when taken orally (Djupesland et al., 2014). A low-dose aspirin for nasal delivery would offer an alternative and effective therapy for the treatment of these disorders and would be safer than daily, oral aspirin treatment by avoiding exposure to the gastrointestinal system.

Accordingly, there remains a need for use of low-dose aspirin designed for nasal delivery for the treatment of NDs and LSDs without the potential of complicated gastrointestinal side effects.

SUMMARY

One embodiment described herein is a method of delivering acetylsalicylic acid to a subject comprising administering a therapeutically effective amount of acetylsalicylic acid to the subject via nasal delivery, such that acetylsalicylic acid is delivered to the central nervous system.

In one aspect, the therapeutically effective amount of acetylsalicylic acid has a dosage of about 0.1 mg/kg/d to about 30 mg/kg/d.

In another aspect, the formulation of the therapeutically effective amount of acetylsalicylic acid is selected from the group consisting of nasal drops, inhalable powder, a propellant containing aerosol, or a propellant-free inhalable solution. In another aspect, the propellant-free inhalable solution comprises acetylsalicylic acid and water.

In another aspect, the propellant-free inhalable solution is administered to the subject via a nebulizer. In a further aspect, the propellant-free inhalable solution is administered to the subject via inhalation.

In another aspect described herein, the method is used to treat a neurodegenerative disorder in the subject in need thereof. In one aspect the neurodegenerative disorder is selected from the group consisting of Multiple Sclerosis, Experimental Allergic Encephalomyelitis (EAE) Alzheimer's disease, Parkinson's disease, or Huntington's disease. In a further aspect, the method is used to treat a lysosomal storage disorder in the subject in need thereof. In another aspect, the lysosomal storage disorder is selected from the group consisting of Batten disease, Neimann-Pick disease, Krabbe disease, or Tay-Sachs disease.

In another aspect described herein, the administration of a therapeutically effective amount of acetylsalicylic acid results in a reduction of plaque load of at least 50%. In a further aspect described herein, the administration of a therapeutically effective amount of acetylsalicylic acid results in a reduction of demylenation of at least 50%.

In yet another aspect described herein, the acetylsalicylic acid is not exposed to the gastric mucosa.

BRIEF DESCRIPTION OF THE DRAWINGS

FIG. 8A-8C: Nebulization of very low-dose aspirin protects myelin in experimental autoimmune encephalomyelitis (EAE), a mouse model of multiple sclerosis. EAE was induced in female SJL/J mice (4-6 week old) by adoptive transfer of MBP-primed T cells. Mice were treated with 0.2 mg/kg body wt/d and 0.4 mg/kg body wt/d aspirin via nebulization using the Buxco Inhalation Tower from the onset of acute phase. A) Spinal cord sections were immunostained with MBP (red). B) Sections were also stained with Luxol fast blue. Digital images were collected under bright field setting using a 40× objective. Demyelination was represented quantitatively (C). Data are expressed as the mean±SEM of five different mice per group. $^a p<0.001$ vs non-Tg; $^b p<0.001$ vs. FAD5×.

DETAILED DESCRIPTION

The embodiments disclosed below are not intended to be exhaustive or to limit the scope of the disclosure to the precise form in the following description. Rather, the embodiments are chosen and described as examples so that others skilled in the art may utilize its teachings.

The present disclosure relates to methods of delivering acetylsalicylic acid via nasal delivery to a subject, such that the acetylsalicylic acid is delivered to the central nervous system. Also disclosed herein are methods for the treatment of neurodegenerative and lysosomal storage disorders.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Treating", "treat", or "treatment" as used herein, means an alleviation of symptoms associated with a disorder or disease, or halt of further progression or worsening of those symptoms, or prevention or prophylaxis of the disease or disorder. For example, within the context of this disclosure, successful treatment may include prevention of a neurodegenerative disease, an alleviation of symptoms related to neurodegenerative disease or a halting in the progression of a disease such as a neurodegenerative disease. As used herein, a control for measuring the treatment relative it a control is a subject that has not received the therapeutic agent.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Provided herein are methods of delivering acetylsalicylic acid to a subject comprising administering a therapeutically effective amount of acetylsalicylic acid via nasal delivery such that the drug is delivered to the central nervous system.

Modes of Delivery

Methods of delivering acetylsalicylic acid include any number of modes of administering acetylsalicylic acid or pharmaceutical compositions of acetylsalicylic acid to the nose. Modes of administration may include delivery of liquid or powder formulations of pharmaceutical compositions for nasal administration via either passive of active delivery mechanisms. Liquid formulations, may be delivered through a variety of mechanisms including vaporization through nasal inhalation, hand actuated nasal devices and mechanical spray pumps. Formulations for such delivery mechanisms may be in the form of propellant containing aerosols or propellant-free inhalable solutions. Mechanical spray pumps may be hand actuated, gas driven or electrical, as in the case of electrically powered nebulizers and atomizers. In one aspect described herein, a propellant-free inhalable solution is administered by nebulizer or direct nasal inhalation.

Powder formulations may be delivered though mechanical power sprayers, nasal inhalers and nebulizers/atomizers. Prior to delivery, powder formulations may be solubilized in suitable solvents including water and saline solutions. In one embodiment described herein the acetylsalicylic acid may be solubilized in a saline solution.

Pharmaceutical Compositions

Regardless of the type of formulation, aspirin may be incorporated into pharmaceutical compositions suitable for administration to a subject (such as a patient, which may be a human or non-human).

In some embodiments, Aspirin will be employed in the form of salicylic acid acetate also referred to as acetylsalicylic acid (AA).

The pharmaceutical compositions may include a "therapeutically effective amount" or of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of the agent are outweighed by the therapeutically beneficial effects.

In some embodiments, a therapeutically effective amount of AA (in mg/kg/d) may be about 0.01 mg/kg/d to about 500 mg/kg/d, about 0.025 mg/kg/d to about 400 mg/kg/d, about 0.05 mg/kg/d to about 300 mg/kg/d, about 0.075 mg/kg/d to about 200 mg/kg/d, about 1 mg/kg/d to about 100 mg/kg/d, about 1.25 mg/kg/d to about 90 mg/kg/d, about 1.5 mg/kg/d to about 80 mg/kg/d, about 1.75 mg/kg/d to about 70 mg/kg/d, about 2 mg/kg/d to about 60 mg/kg/d, about 2.5 mg/kg/d to about 50 mg/kg/d, about 3 mg/kg/d to about 40 mg/kg/d, about 3.5 mg/kg/d to about 30 mg/kg/d, about 4 mg/kg/d to about 20 mg/kg/d, or about 5 mg/kg/d to about 10 mg/kg/d. In one aspect, the therapeutically effective amount of aspirin may be about 10 mg/kg/d to about 30 mg/kg/d. In another aspect, the therapeutically effective amount of aspirin may be about 1 mg/kg/d to about 50 mg/kg/d. In another aspect, the therapeutically effective amount of aspirin may be about 0.1 mg/kg/d to about 50 mg/kg/d. In yet another aspect, the therapeutically effective amount of aspirin may be about 0.1 mg/kg/d to about 30 mg/kg/d. In liquid formulations, depending on the type of delivery system, in addition to AA, the formulation may include a variety of functional excipients, including solvents and cosolvents such as water or saline solutions; mucoadhesive agents; pH buffers; antioxidants; preservatives; osmolality and tonicity agents; penetration enhancers; suspending agents; and surfactants. The ultimate choice of formulation type and the excipients selected will be driven by the solubility and stability of the AA, as well as the concentration needed to deliver a therapeutic dose. By way of non-limiting example, the formulation may be delivered with a delivery volume that may be about 50-500 µl spray, and in some embodiments about a 100 µl spray.

Inhalable powders may be formulated in any conventional manner, including as a dry powder formulation, a formulation for a pMDI, or an aqueous nebulisable formulation. Powder formulations may also be reconstituted into liquid formulations. Prior to delivery, powder formulations may be solubilized in suitable solvents including water and saline solutions. In one embodiment described herein the acetylsalicylic acid may be solubilized in a saline solution.

Whether using either a liquid or powder AA formulation, active or passive delivery, by administering to the nose, the AA is not exposed to the gastric mucosa and thus avoids the side effects associated with oral AA formulations.

Delivery to the Central Nervous System

In some embodiments described herein, the method for delivering AA via nasal delivery is such that the AA is ultimately delivered to the central nervous system. Without being bound to any theory, it is believed that nasal administration of AA formulations can take advantage of "nose-to-brain" (N2B) transport systems (Djupesland, 2013) in which several possibilities exist for bypassing the blood-brain-barrier for direct delivery to the brain. These include the draining of drugs absorbed in the nasal mucosa into the sinus and eventually to the carotid artery, where a "counter-current transfer" from venous blood to the brain may occur. Lymphatic drainage into the perivascular space from the olfactory trigeminal nerves between the central nervous system (CNS) have also been postulated as the mechanism of N2B transport.

Neurodegenerative and Lysosomal Storage Disorders

Nasal delivery for targeting the central nervous system is ideal for the treatment of neurodegenerative and lysosomal storage disorders. In one aspect, the method for delivering AA via nasal delivery to the central nervous system is for the treatment of a neurodegenerative disorder (ND). The neurodegenerative disorder may be Alzheimer's disease (AD), Huntington's disease, Amyotrophic lateral sclerosis (ALS), Parkinson's disease, including Parkinson's plus diseases such as multiple system atrophy (MSA), multiple sclerosis (MS) (including the animal model of MS, experimental allergic encephalomyelitis (EAE) and other human demyelinating diseases), progressive supranuclear palsy (PSP), corticobasal degeneration (CBD) or dementia with Lewy bodies (DLB). Batten disease is the most common form of a group of disorders called the neuronal ceroid lipofuscinoses (NCL). The neurodegenerative disease may be caused by a lysosomal storage disorder. In another aspect described herein the method for delivering AA via nasal delivery to the central nervous system is for the treatment of lysosomal storage disorders (LSD). The lysosomal storage disorder may be, for example, Tay-Sach's disease, Fabry disease, Niemann-Pick disease, Krabbe disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, or Galactosialidosis.

The present disclosure has multiple aspects, illustrated by the following non-limiting examples.

EXAMPLES

Studies were performed to evaluate the effects of low-dose aspirin nebulization in animal models of mice with multiple sclerosis (MS) and Alzheimer's disease (AD).

Aspirin Preparation:

Oral tablets of baby aspirin with a standard dosage of 81 mg were solubilized in hot double distilled water and cooled to room temperature. This liquid formulation was made fresh every week. In mice, an aspirin dose of 1 mg/kg body wt/d aspirin is equivalent to "Baby Aspirin" (81 mg tablet per adult).

Figure 1A:
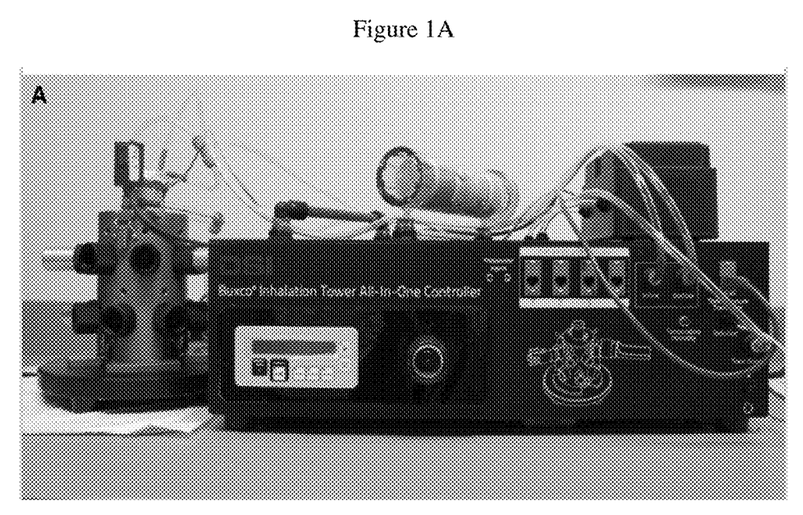
FIG. 1A-1B. 1A) A Buxco Inhalation Tower All-In-One Controller by DSI™ was used for air supply for nebulization. 1B) A whole body chamber was fitted with an Aeroneb® Ultrasonic Nebulizer supplied with air from a Buxco bias flow pump.
Figure 1B:
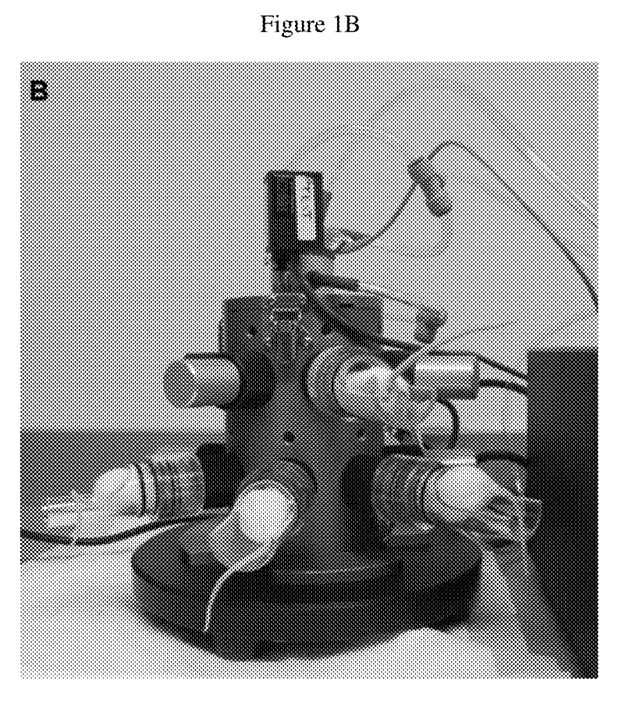

Nebulization:

A Buxco Inhalation Tower All-In-One Controller by DSI™ was used for air supply for nebulization (FIG. 1A). A whole body chamber was fitted with an Aeroneb® Ultrasonic Nebulizer (FIG. 1B) supplied with air from a Buxco bias flow pump. Mice were allowed to nebulize aspirin at doses of 0.25 or 0.5 mg/kg body wt/d (solubilized in a volume of 100 µl double-distilled water/mouse) for 3 min. Therefore, control group of mice also received 100 µl water by nebulization.

Example 1

Figure 2A:
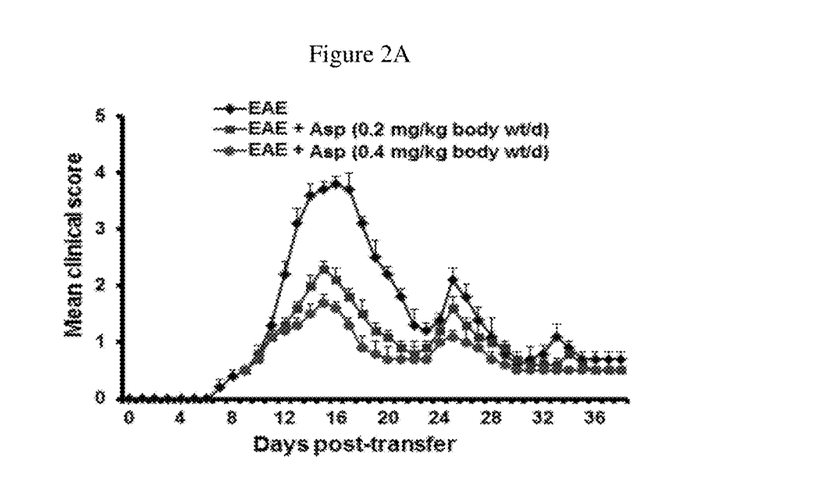
FIG. 2A-2C. Nebulization of low-dose aspirin reduced clinical symptoms of experimental allergic encephalomyetis (EAE) in female SJL/J mice. 2A) EAE was induced in 4-5 week old female SLJ/mice by adoptive transfer of myelin basic protein (MBP) primed T cells and from 9 days post-transfer (dpt), mice were treated with different doses of aspirin once daily for nebulization. Mice (n=6 per group in two independent experiments) were scored daily. On 16 dpt (acute phase), mice were examined for grip test (2B) and rotorod (2C). Results are presented as mean±SEM of six (6) mice per group. $^a p<0.001$ vs control; $^b p<0.001$ vs EAE by two-samples t-tests.
Figure 2B:
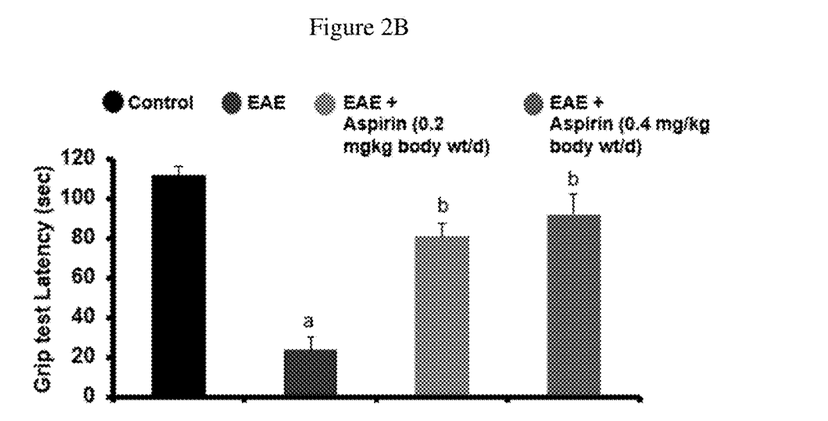
Figure 2C:
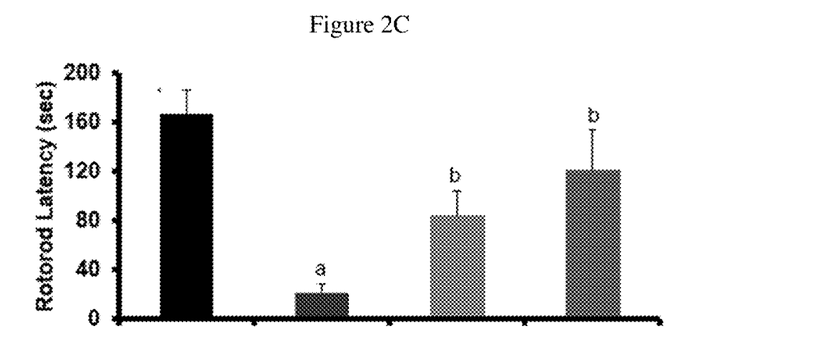

Low Dose Aspirin Nebulization in Mice with Multiple Sclerosis (MS):

Experimental allergic encephalomyelitis (EAE) is an animal model of MS, the most common human demyelinating disease. RR-EAE was induced in female SJL/J mice by adoptive transfer of myelin based protein (MBP) primed T cells (FIG. 2A). As expected, induction of EAE reduced grip test (FIG. 2B) and rotorod (FIG. 2C) performances of mice. Mice were then nebulized with aspirin (0.2 and 0.4 mg/kg body wt/d in a volume of 100 µl/mouse) from 9 days post-transfer (dpt) of MBP-primed T cells. The control EAE group were treated with only water via nebulization. A dose of 0.2 mg/kg body wt/d aspirin equates to approximately 16 mg per adult. Clinical symptoms were monitored every day until 38 dpt. At both 0.2 and 0.4 mg/kg body wt/d doses used, aspirin nebulization strongly inhibited clinical manifestations of adoptively-transferred EAE (FIG. 2A) and significantly improved grip test (FIG. 2B) and rotorod (FIG. 2C) activities of EAE mice. A dosage of 0.2 mg/kg body wt/d in mice equates to 16.2 mg dosage aspirin in humans which is only $\frac{1}{5}^{th}$ the dosage of "Baby Aspirin" in humans. This shows that nebulization of very low-dose aspirin is capable of suppressing EAE in mice. Moreover, by nebulization it is possible to bypass the stomach, thereby reducing the chance of gastrointestinal problems.

Figure 3A:
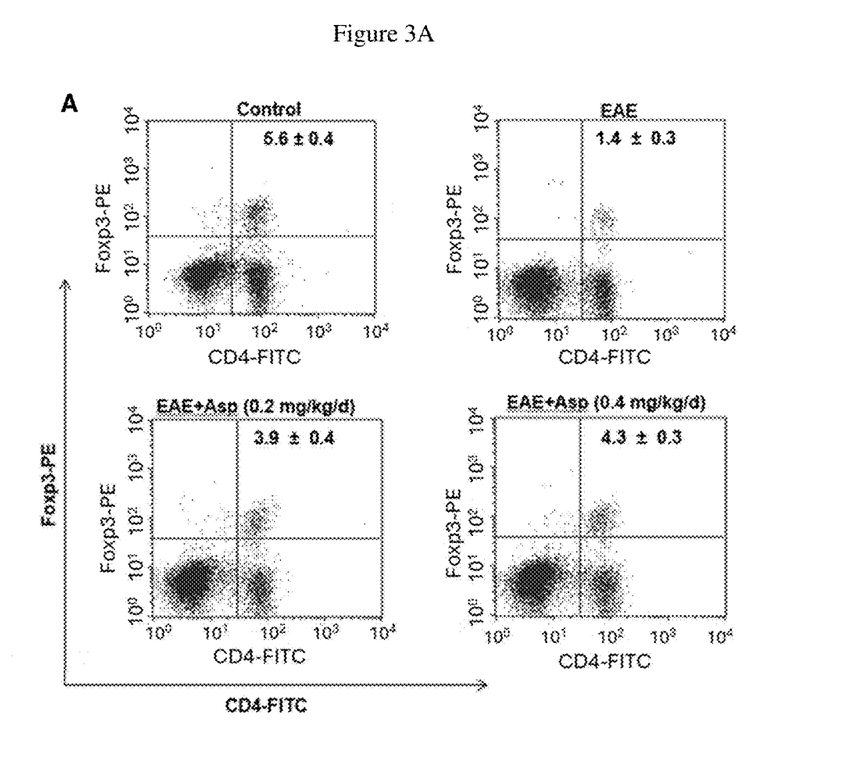
FIG. 3A-3B. Nebulization of low-dose aspirin improves regulatory T cells (Tregs) in vivo in mice with adoptive transfer EAE. Lymph node cells of control, EAE (16 dpt) and low doses of aspirin-treated EAE mice (16 dpt receiving 0.2 and 0.4 mg/kg body wt/d aspirin in 100 µl water from 9 dpt via nebulization) were analyzed by fluorescence activated cell sorting (FACS) for Foxp3 and CD4 (3A). The mean fluorescence intensity (MFI) of Foxp3 in CD4+ population was calculated by using CellQuest software (3B). Data were mean±SEM of four mice per group. $^a p<0.001$ vs control; $^b p<0.001$ vs EAE by two-samples t-tests.
Figure 3B:
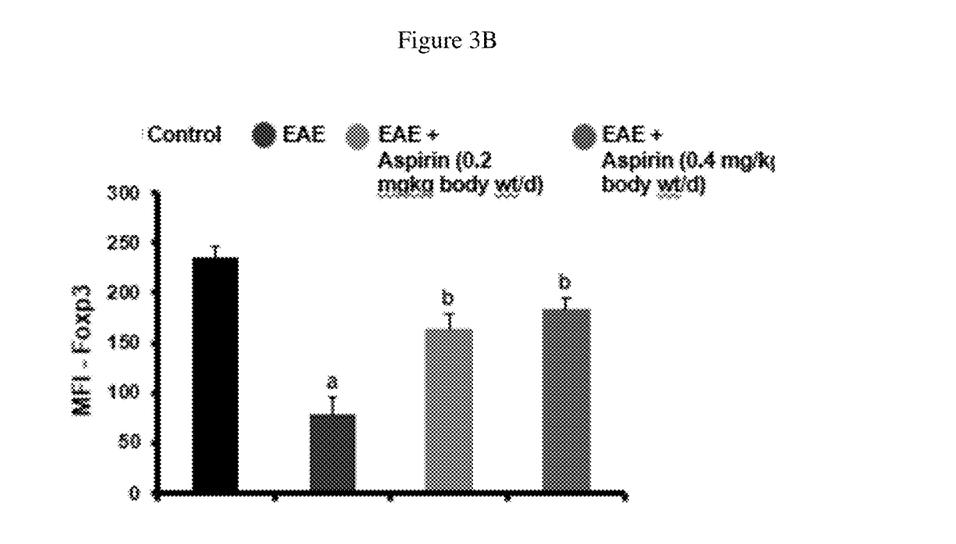

Aspirin Nebulization Improves Regulatory T Cells (Tregs) In Vivo in EAE Mice:

Tregs are most important immunomodulatory subtype of T lymphocytes (Sakaguchi, 2005; Sakaguchi and Powrie, 2007) that are known to suppress EAE and MS. Nebulization of aspirin was further investigated to determine whether nebulization was capable of enriching Tregs in vivo in EAE mice. EAE mice receiving aspirin nebulization from 9 dpt were sacrificed on 16 dpt, followed by analysis of Tregs in lymph node cells (LNC). Foxp3 protein is currently considered as the most important marker of Tregs and by dual fluorescence-activated cell sorting (FACS) staining, we found decrease in CD4$^+$Foxp3$^+$ Tregs in LNC of EAE mice (FIG. 3A-B). However, nebulization of EAE mice with aspirin at both 0.2 and 0.4 mg/kg body wt/d doses protected CD4+Foxp3+ Tregs (FIG. 3A-B).

Figure 4A:
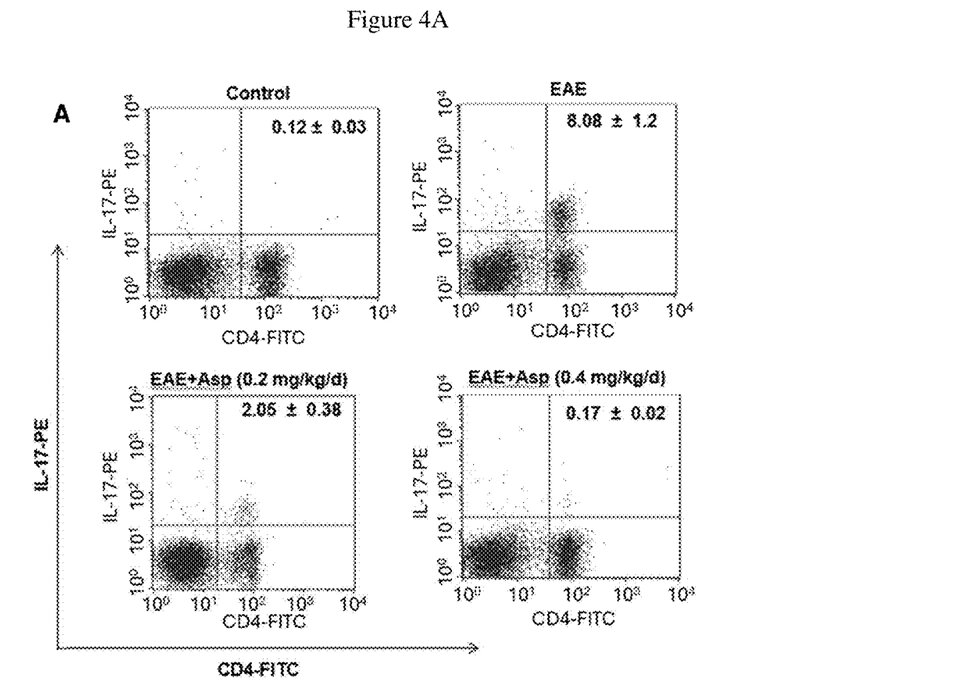
FIG. 4A-4B. Nebulization of low-dose aspirin suppresses the Th17 response in vivo in mice with adoptive transfer EAE. Lymph node cells of control, EAE (16 dpt) and low doses of aspirin-treated EAE mice (16 dpt receiving 0.2 and 0.4 mg/kg body wt/d aspiring in 100 µl water from 9 dpt via nebulization) were analyzed by FACS for IL-17 and CD4 (4A). The MFI of IL-17 in CD4+ population was calculated by using CellQuest software (4B). Data were mean±SEM of four mice per group. $^a p<0.001$ vs control; $^b p<0.001$ vs EAE by two-samples t-tests.
Figure 4B:
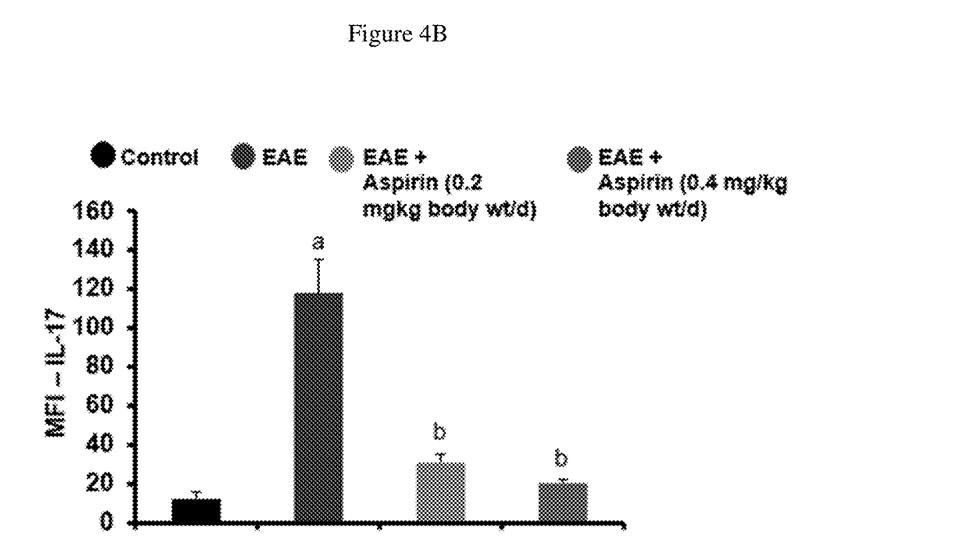

Aspirin Nebulization Inhibits the Th17 Response In Vivo in EAE Mice:

T helper cell 17 (Th17) cells are considered to play a more important role than Th1 cells in the disease process of EAE and MS (El-behi et al., 2010). Since aspirin nebulization enriched Tregs, aspirin nebulization was tested to determine if aspirin nebulization was capable of suppressing Th17 response in vivo in EAE mice. Th17 cells are characterized by expression of IL-17 (Shi et al., 2008). FACS analysis also demonstrated upregulation of CD4+IL-17+ T cells in LNC of EAE mice as compared to normal mice (FIG. 4A). However, nebulization of EAE mice with aspirin led to the suppression of the CD4+IL-17+ T cell population in LNC (FIG. 4A). This is also corroborated by mean fluorescence intensity (MFI) analysis of IL-17 within the CD4+ population (FIG. 4A). These results clearly show that nebulization of low dose of aspirin is capable of reducing Th17 response.

Example 2

Figure 5A:
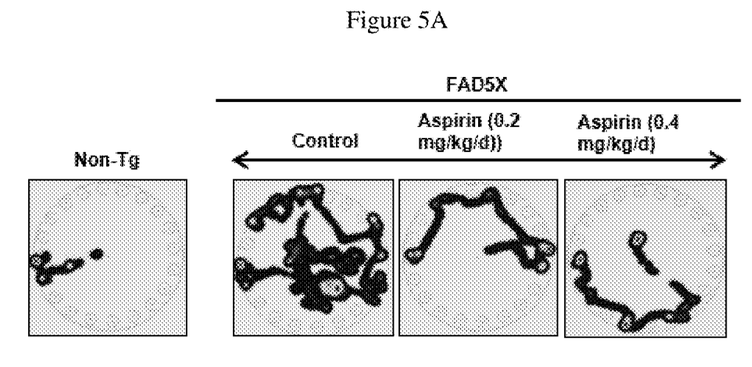
FIG. 5A-5E. Nebulization of low-dose aspirin protects memory in the FAD5× mouse model of AD. Six to seven-month old FAD5× mice were treated with low doses (0.2 and 0.4 mg/kg body wt/d) of aspirin via nebulization. After 30 days of treatment, hippocampus-dependent spatial behavior was monitored by Barnes maze. 5A) Representative heat maps summarizing the overall activity of mice on the apparatus recorded with a Noldus camera and visualized by Ethovision XT software. 5B) Latency and 5C) number of errors made by all groups of mice. Context-dependent hippocampal behavior was analyzed by T-maze. 5D) Number of positive turns and 5E) number of negative turns of all groups of mice on an appetitive T-maze conditioning task were manually recorded. Results are presented as mean±SEM of 5 mice per group. $^a p<0.001$ vs non-Tg; $^b p<0.001$ vs FAD5×; $^c p<0.01$ vs non-Tg; $^d p<0.05$ vs FAD5×.
Figure 5B:
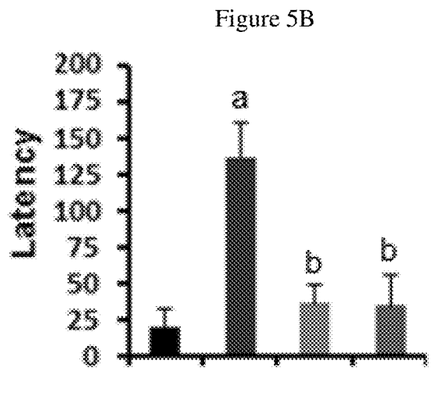
Figure 5C:
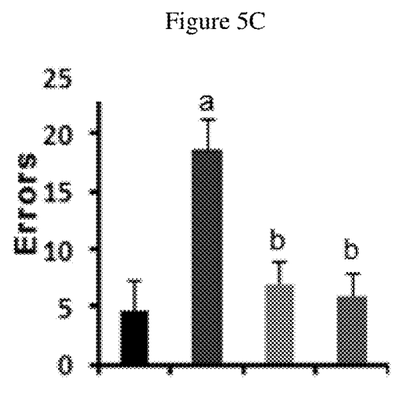

Low-Dose Aspirin Nebulization in Mice with Alzheimer's Disease (AD):

Oral administration of aspirin at a dose of 2 mg/kg body wt/d has been found to protect memory and learning in the FAD5× mouse model of AD (Patel et al., 2018). Therefore, the effect of low-dose aspirin nebulization on hippocampus-dependent behaviors in FAD5× mice was investigated. Hippocampus-dependent spatial learning and cognitive behavior can be reliably monitored in the Barnes maze test (Roy et al., 2013; Roy et al., 2015). As expected and reported in earlier studies (Rangasamy et al., 2015; Roy et al., 2015), FAD5× mice displayed decreased spatial behaviors indicated by the heat map (FIG. 5A), latency (FIG. 5B) and errors (FIG. 5C) as compared to age-matched non-transgenic mice. However, aspirin nebulization at both the doses significantly improved latency (FIG. 5B) and decreased errors (FIG. 5C) in FAD5× mice.

Figure 5D:
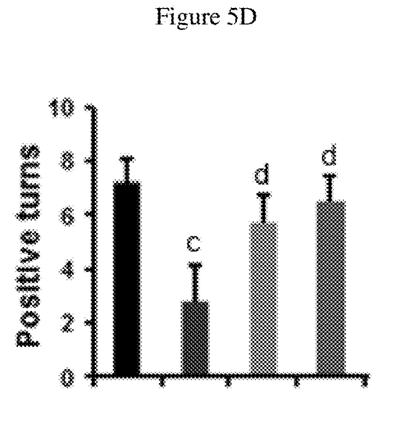
Figure 5E:
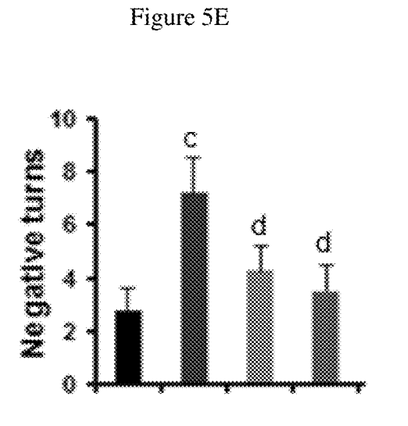

T-maze apparatus monitors context-dependent hippocampal behavior, which may be a better index to test cognition in mice. As expected, untreated FAD5× mice exhibited less number of positive turns (FIG. 5D) and greater number of negative turns (FIG. 5E) than age-matched non-Tg mice in T-maze apparatus. However, similar to that observed with Barnes maze, nebulization of low doses of aspirin improved the performance of FAD5× mice on T maze as evident by increase in positive turns (FIG. 5D) and decrease in negative turns (FIG. 5E).

Example 3

Figure 6A:
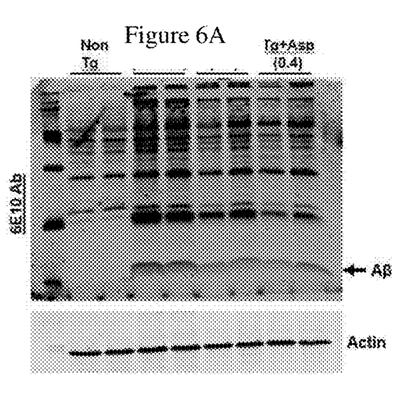
FIG. 6A-6D: Nebulization of very low-dose aspirin lowers cerebral plaque load in an animal model of AD. Six-month old FAD5× transgenic mice were treated with 0.2 mg/kg body wt/d and 0.4 mg/kg body wt/d aspirin via nebulization using the Buxco Inhalation Tower. After 30 days of treatment, Aβ levels were monitored in hippocampal extracts by Western blot analysis (A & C) and densitometric analysis (B & D) using 6E10 (A & B) and 82E1 (C & D) antibodies. Actin was used as loading control. Results are presented as mean±SEM of 4 mice per group. $^a p<0.001$ vs non-Tg; $^b p<0.001$ vs. FAD5×.
Figure 6B:
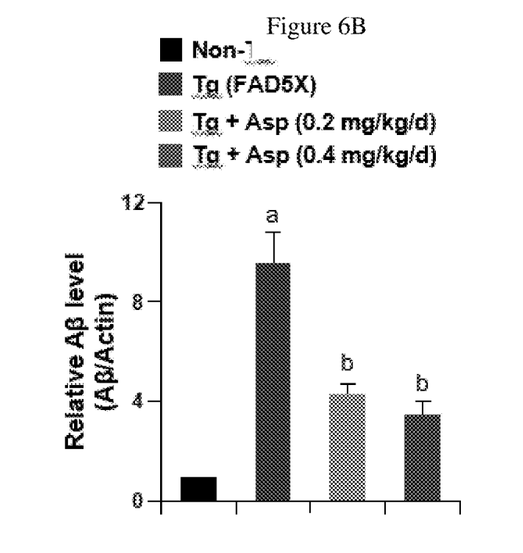
Figure 6C:
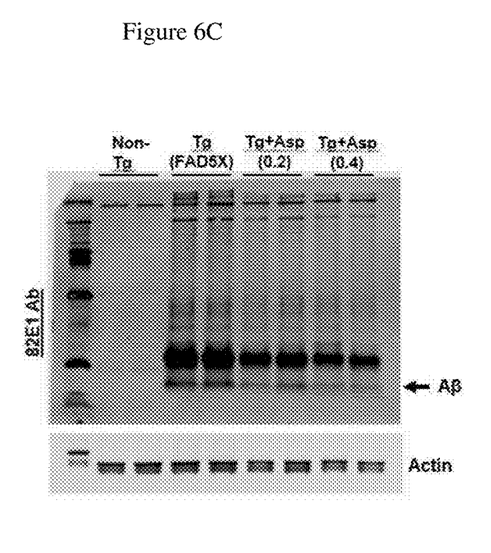
Figure 6D:
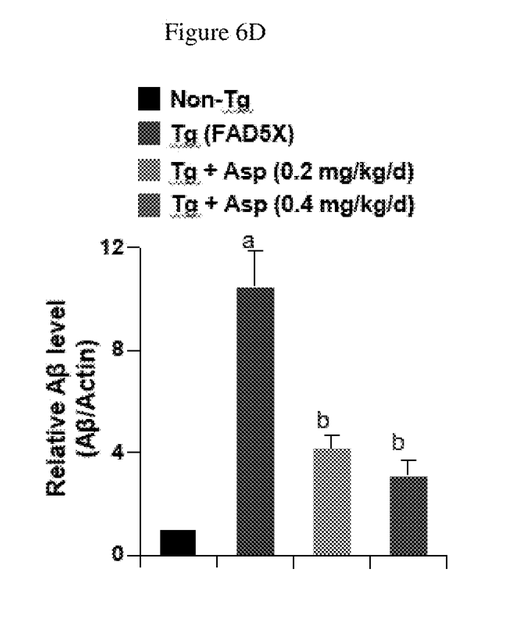

Nebulization of Low-Dose Aspirin Reduces the Amyloid Burden in the Hippocampus of 5×FAD Mice:

To explore whether nebulization of very low-dose aspirin was capable of reducing the amyloid load in the hippocampus, the most affected brain region in AD, of FAD5× (Tg) mice, the following experiment was performed. Immunoblot analysis using Aβ specific antibody 6E10 showed a remarkable increase in the Aβ levels in the hippocampal homogenates from Tg mice as compared to non-Tg mice (FIG. 6A). However, nebulization of aspirin at 0.2 mg/kg body weight/d and 0.4 mg/kg body weight/d significantly reduced the level of Aβ in the hippocampus of Tg mice (FIG. 6A-B). These results were further confirmed by 82E1, another Aβ-specific antibody (FIG. 6C-D). The 82E1 is known to detect both soluble and fibrillar human Aβ to a similar degree.

Figure 7A:
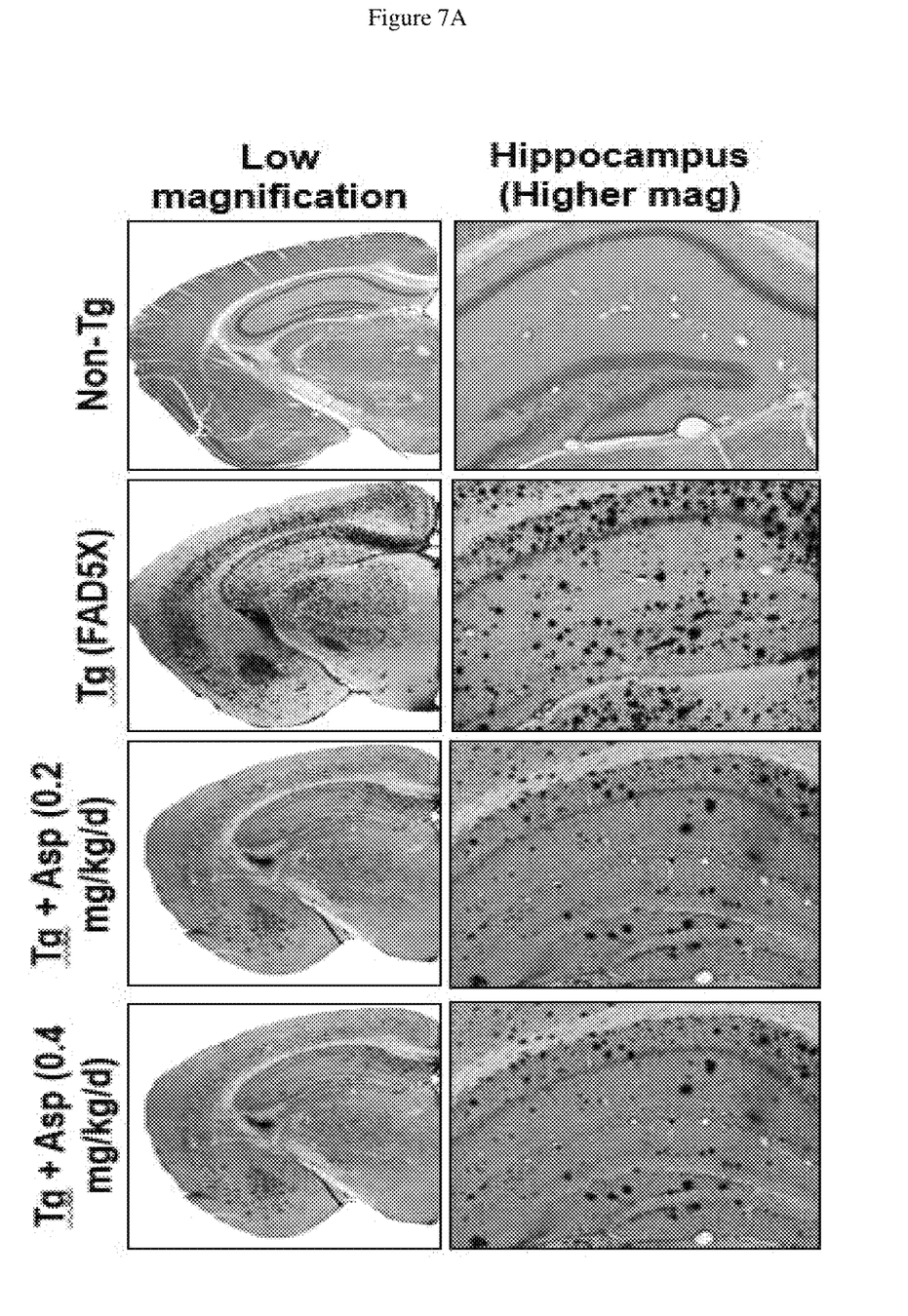
FIG. 7A-7B: Nebulization of very low-dose aspirin lowers cerebral plaque load in an animal model of AD. Six-month old FAD5× transgenic mice were treated with 0.2 mg/kg body wt/d and 0.4 mg/kg body wt/d aspirin via nebulization using the Buxco Inhalation Tower. After 30 days of treatment, A) diaminobenzidine (DAB) staining was performed in hippocampal sections using 6E10 antibody. B) Quantification of number of plaques in the hippocampus relative to nontransgenic. Two sections (two images per section) of each of five mice per group were used in counting. All data are represented as mean±SEM. $^a p<0.001$ vs non-Tg; $^b p<0.001$ vs. FAD5×.
Figure 7B:
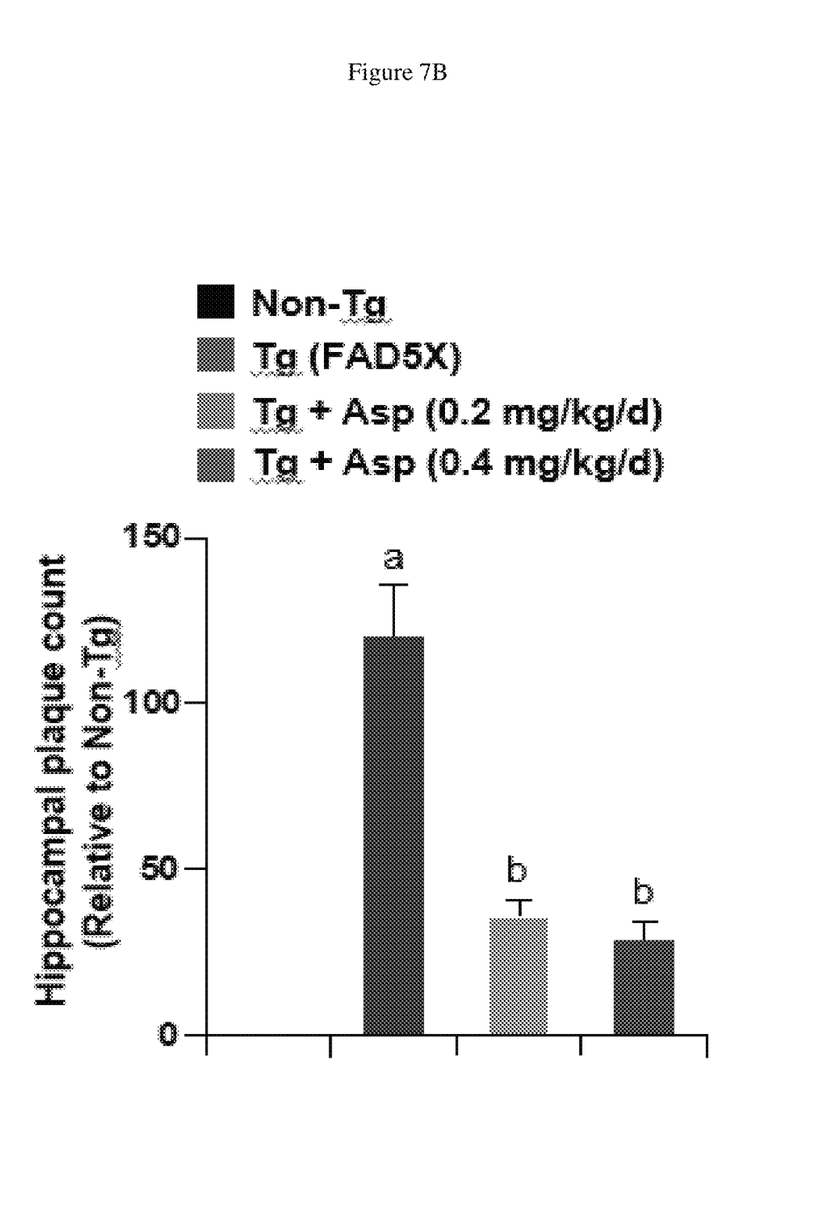

Next, in order to check the amyloid deposition in the brain, hippocampal sections were labeled with 6E10 antibody by diaminobenzidine immunostaining. Parallel to the immunoblot results, there was marked abundance of Aβ immunoreactive plaques in the hippocampus of Tg mice (FIG. 7A-B). However, treatment of Tg mice with low doses of aspirin was capable of decreasing the plaque load (FIG. 7A-B).

Example 4

Figure 8A:
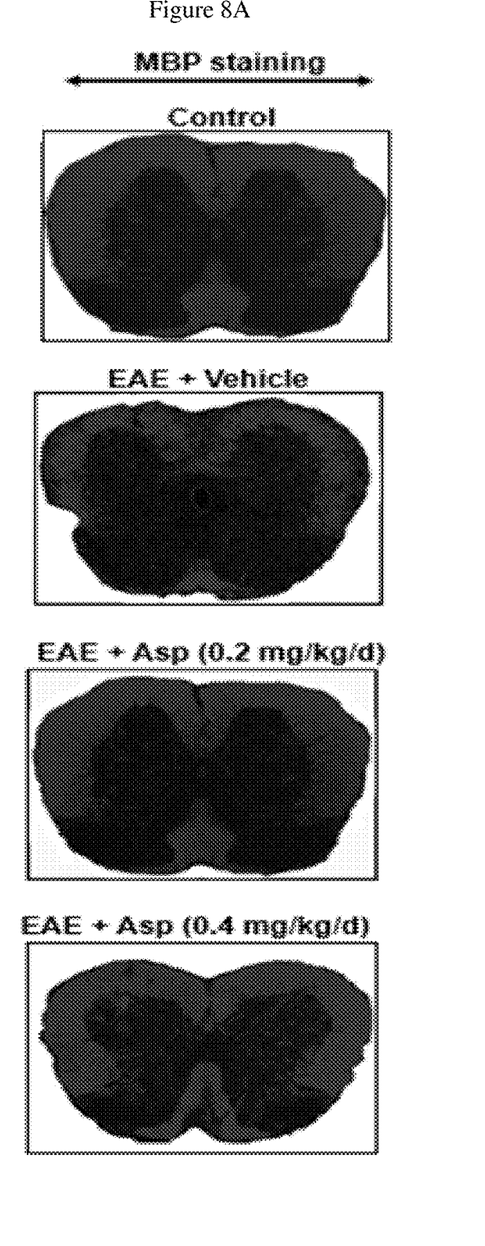
Figure 8B:
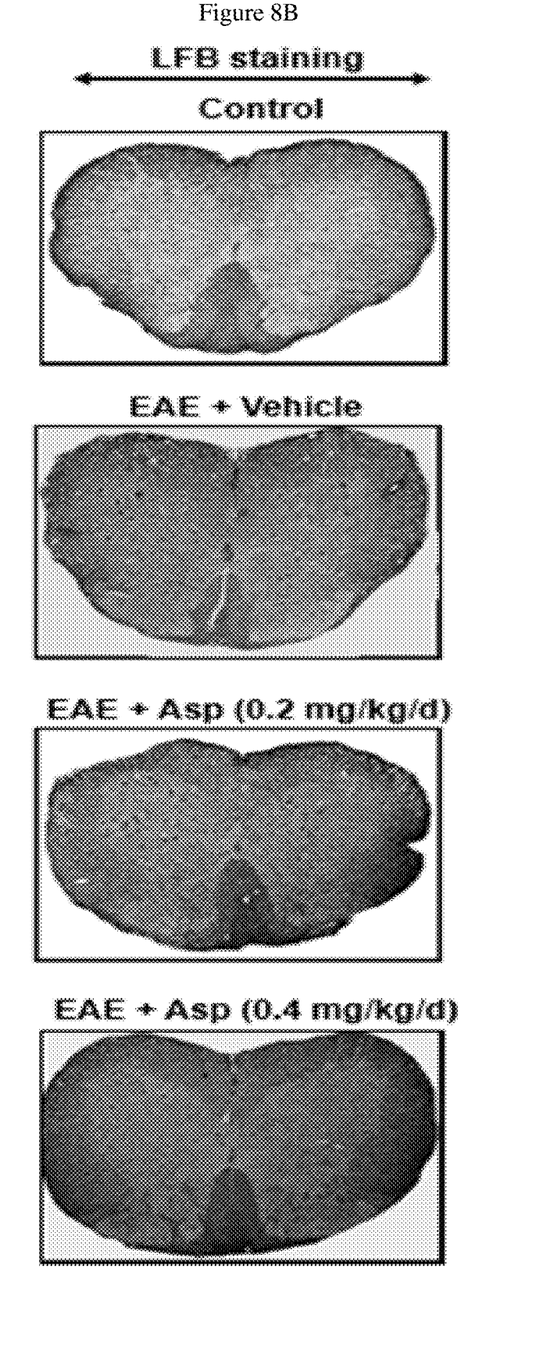
Figure 8C:
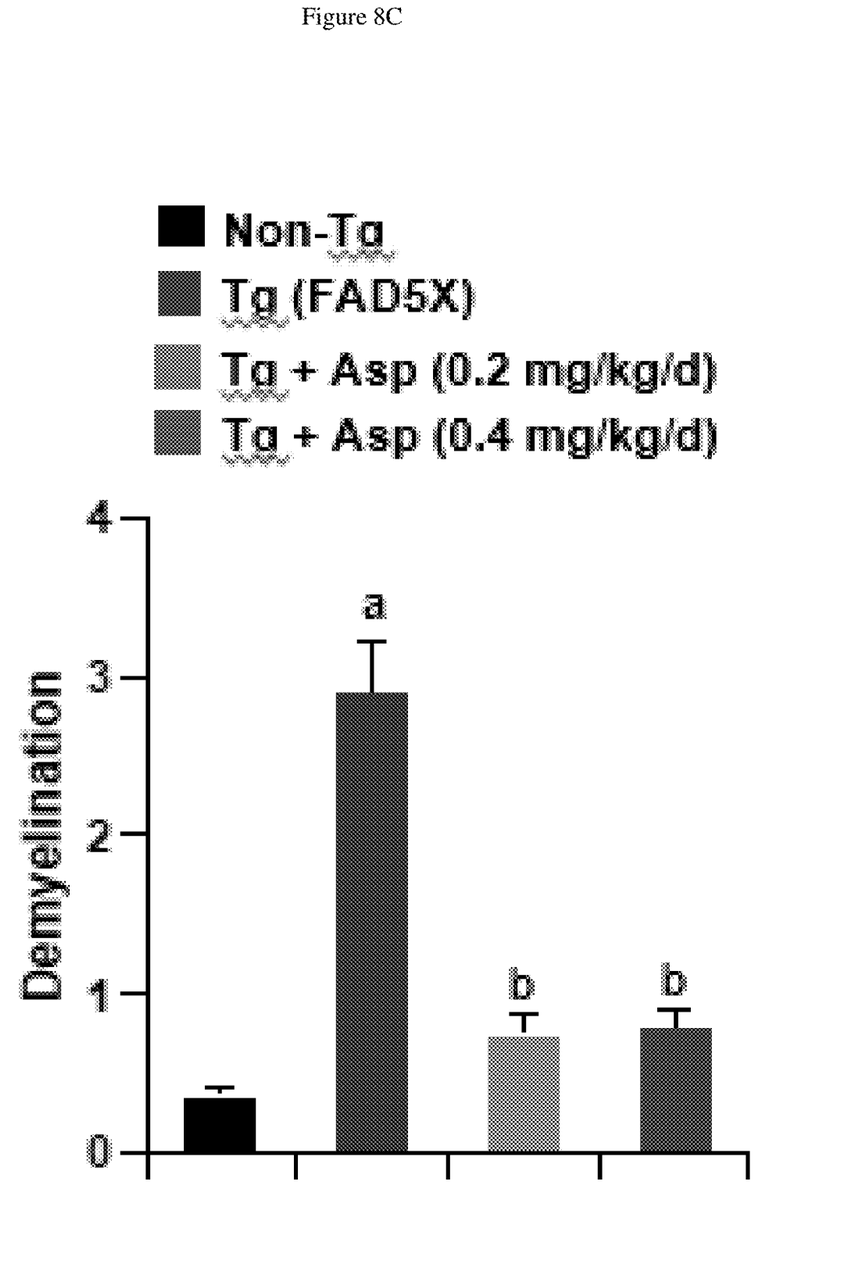

Nebulization of Low-Dose Aspirin Suppresses Demyelination in Spinal Cord of Experimental Autoimmune Encephalomyelitis (EAE) Mice:

EAE is an animal model of human demyelinating disease multiple sclerosis (MS). It was determined whether aspirin nebulization decreased demyelination in mice with EAE. To examine demyelination, spinal cord sections were stained with MBP, a major component of myelin. Moreover, spinal cord sections were also stained with luxol fast blue (LFB), which reacts with myelin. As evident from MBP immunostaining (FIG. 8A) and LFB staining (FIG. 8B), there were widespread demyelination zones in the white matter in mice with EAE. However, aspirin nebulization at both doses (0.2 and 0.4 mg/kg body wt/d) prevented the loss of myelin in the spinal cords of mice with EAE (FIG. 8A-B).

All publications, patents and patent applications cited in this specification are incorporated herein by reference for the teaching to which such citation is used.

The specific responses observed may vary according to and depending on the particular type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

REFERENCES

Aubin N., Curet O., Deffois A., Carter C. (1998) Aspirin and salicylate protect against MPTP-induced dopamine depletion in mice. *J Neurochem*, 71, 1635-1642.

Berk M., Dean O., Drexhage H., McNeil J. J., Moylan S., O'Neil A., Davey C. G., Sanna L., Maes M. (2013) Aspirin: a review of its neurobiological properties and therapeutic potential for mental illness. *BMC Med*, 11, 74.

Chandra, S., Malabendu J., Pahan K. (2018) Aspiring induces Lysosomal biogenesis and attenuates Amyloid plaque pathology in a mouse model of Alzheimer's disease via a PPARα. *J Neuroscience*, 0054-18; DOI: https://doi.org/10.1523/JNEUROSCI.0054-18.2018.

Dai Y., Ge J. (2012) Clinical use of aspirin in treatment and prevention of cardiovascular disease. *Thrombosis.* 2012; 2012: 245037. Published online 2011 Nov. 24. doi: [10.1155/2012/245037].

De Duve, C. and Wattiaux, R. (1966) Functions of lysosomes. *Annu Rev Physiol*, 28, 435-492.

Djupesland, P. G., Messina J. C., Mahmoud, R. A. (2014) The nasal approach to delivering treatment for brain diseases: an anatomic, physiologic, and delivery technology overview. *Therapeutic Delivery*, 5(6), 709-733.

Djupesland, P. G. (2013) Nasal drug delivery devices: characteristics and performance in a clinical perspective—a review. *Drug Deliv Transl Res*. 3(1), 42-62.

El-behi, M., Rostami, A., and Ciric, B. (2010) Current views on the roles of Th1 and Th17 cells in experimental autoimmune encephalomyelitis. *J Neuroimmune Pharmacol*, 5, 189-197.

Green G A (2001) Understanding NSAIDs: from aspirin to COX-2. *Clin Cornerstone*, 3, 50-60.

Lanas A., and Scheiman J. (2007) Low-dose aspirin and upper gastrointestinal damage: epidemiology, prevention and treatment. *Curr Med Res Opin.*, 23(1), 163-73.

Mondal, S., Jana, M., Dasarathi, S., Roy, A., and Pahan, K. (2018) Low-dose aspirin ameliorates experimental allergic encephalomyelitis through interleukin-11-mediated protection of regulatory T cells. Sci. Signal. (In press).

Moyad M. A. (2001) An introduction to aspirin, NSAids, and COX-2 inhibitors for the primary prevention of cardiovascular events and cancer and their potential preventive role in bladder carcinogenesis: part II. *Semin Urol Oncol*, 19, 306-316.

Nilsson S. E., Johansson B., Takkinen S., Berg S., Zarit S., McCleam G., Melander A. (2003) Does aspirin protect against Alzheimer's dementia? A study in a Swedish population-based sample aged > or =80. *Eur J Clin Pharmacol*, 59, 313-319.

Patel, D., Roy, A., Kundu, M., Jana, M., Luan, C. H., Gonzalez, F. J., and Pahan, K. (2018). Aspirin binds to PPARα to stimulate hippocampal plasticity and protect memory. *Proc Natl Acad Sci*, 115, E7408-E7417.

Rangasamy, S. B., Corbett, G. T., Roy, A., Modi, K. K., Bennett, D. A., Mufson, E. J., Ghosh, S., and Pahan, K. (2015) Intranasal Delivery of NEMO-Binding Domain Peptide Prevents Memory Loss in a Mouse Model of Alzheimer's Disease. *J Alzheimers Dis*, 47, 385-402.

Rangasamy, S. B., Dasarathi, S., Pahan, P., Jana, M., and Pahan, K. (2018) Low-dose aspirin upregulates tyrosine hydroxylase and increases dopamine production in dopaminergic neurons: Implications for Parkinson's disease. *J Neuroimmune Pharmacol.* (In press; DOI: 10.1007/s11481-018-9808-3).

Rizwan S., Idrees A., Ashraf M., Ahmed T. (2016) Memory-enhancing effect of aspirin is mediated through opioid system modulation in an AlCl3-induced neurotoxicity mouse model. *Exp Ther Med*, 11, 1961-1970.

Rothwell P. M., Wilson M., Price J. F., Belch J. F., Meade T. W., Mehta Z. (2012) Effect of daily aspirin on risk of cancer metastasis: a study of incident cancers during randomised controlled trials. *Lancet*, 379, 1591-1601.

Roy, A., Jana, M., Corbett, G. T., Ramaswamy, S., Kordower, J. H., Gonzalez, F. J., and Pahan, K. (2013) Regulation of cyclic AMP response element binding and hippocampal plasticity-related genes by peroxisome proliferator-activated receptor alpha. *Cell Rep*, 4, 724-737.

Roy, A., Jana, M., Kundu, M., Corbett, G. T., Rangaswamy, S. B., Mishra, R. K., Luan, C. H., Gonzalez, F. J., and Pahan, K. (2015) HMG-CoA Reductase Inhibitors Bind to PPARα to Upregulate Neurotrophin Expression in the Brain and Improve Memory in Mice. *Cell Metab*, 22, 253-265.

Sakaguchi, S. (2005) Naturally arising Foxp3-expressing CD25+CD4+ regulatory T cells in immunological tolerance to self and non-self. *Nat Immunol*, 6, 345-352.

Sakaguchi, S., and Powrie, F. (2007) Emerging challenges in regulatory T cell function and biology. *Science*, 317, 627-629.

Sostres, C., Lanas, Al. (2011) Gastrointestinal effects of aspirin. *Nat Rev Gastroenterol Hepatol*, 8(7), 385-94.

Shi, G., Cox, C. A., Vistica, B. P., Tan, C., Wawrousek, E. F., and Gery, I. (2008) Phenotype switching by inflammation-inducing polarized Th17 cells, but not by Th1 cells. *J Immunol*, 181, 7205-7213.

I claim:

1. A method of treating a neurodegenerative disorder in a subject in need thereof, the method comprising administering a therapeutically effective amount of acetylsalicylic acid to the subject via nasal delivery, wherein the therapeutically effective amount is 0.1 mg/kg/d to 1 mg/kg/d of acetylsalicylic acid and wherein the neurodegenerative disorder is selected from the group consisting of Multiple Sclerosis, Experimental Allergic Encephalomyelitis (EAE), Alzheimer's disease, Parkinson's disease, and Huntington's disease.

2. The method of claim 1, wherein the acetylsalicylic acid is formulated to be a propellant-free inhalable solution.

3. The method of claim 2, wherein the propellant-free inhalable solution is administered to the subject via a nebulizer.

4. The method of claim 2, wherein the propellant-free inhalable solution is administered to the subject via nasal inhalation.

5. A method of treating a lysosomal storage disorder in a subject in need thereof, the method comprising administering a therapeutically effective amount of acetylsalicylic acid to the subject via nasal delivery, wherein the therapeutically effective amount is 0.1 mg/kg/d to 1 mg/kg/d of acetylsalicylic acid and wherein the lysosomal storage disorder is selected from the group consisting of Batten disease, Neimann-Pick disease, Krabbe disease, and Tay-Sachs disease.

6. The method of claim 5, wherein the acetylsalicylic acid is formulated to be a propellant-free inhalable solution.

7. The method of claim 6, wherein the propellant-free inhalable solution is administered to the subject via a nebulizer.

8. The method of claim 6, wherein the propellant-free inhalable solution is administered to the subject via inhalation.

* * * * *